United States Patent
West

[11] Patent Number: 5,872,454
[45] Date of Patent: Feb. 16, 1999

[54] CALIBRATION PROCEDURE THAT IMPROVES ACCURACY OF ELECTROLYTIC CONDUCTIVITY MEASUREMENT SYSTEMS

[75] Inventor: Steven J. West, Hull, Mass.

[73] Assignee: Orion Research, Inc., Beverly, Mass.

[21] Appl. No.: 957,527

[22] Filed: Oct. 24, 1997

[51] Int. Cl.$^6$ ................................................ G01N 27/02

[52] U.S. Cl. .................... 324/439; 324/444; 324/446; 73/1.02; 702/85

[58] Field of Search .................... 324/601, 425, 324/439, 441, 444, 446, 470, 721, 722, 713, 717; 204/400, 401, 406, 407; 205/81; 73/1.01, 1.02; 702/85.86, 100, 104

[56] References Cited

U.S. PATENT DOCUMENTS

| | | | |
|---|---|---|---|
| 3,924,175 | 12/1975 | Wilson | 324/444 |
| 4,119,909 | 10/1978 | DeBerry | 324/439 |
| 4,553,094 | 11/1985 | Gehrke | 324/225 |
| 4,713,618 | 12/1987 | Carlson et al. | 204/400 |
| 4,751,466 | 6/1988 | Colvin et al. | 324/444 |
| 4,823,087 | 4/1989 | Sugimori | 324/439 |
| 5,260,663 | 11/1993 | Blades | 324/439 |
| 5,266,899 | 11/1993 | Bull et al. | 324/439 |
| 5,504,430 | 4/1996 | Anderson | 324/439 |

*Primary Examiner*—Diep N. Do
*Attorney, Agent, or Firm*—Ernest V. Linek; Dike, Bronstein, Roberts & Cushman, LLP

[57] ABSTRACT

Disclosed is a two-point calibration procedure, that when used with a mathematical algorithm, improves the accuracy of electrolytic conductivity measurements by correcting for non-linear behavior of conductivity cells. Unlike purely mathematical means of correcting for non-linearity which may use second or higher order equations, this algorithm has the following advantages: it is based on an analysis of the physical phenomena which are responsible for non-linearity; it yields one unique solution, i.e., it uses an equation that has only one root; and it yields diagnostic information concerning the behavior of the cell. A conductivity system utilizing the described algorithm was built and tested and led to the development of the following enhancements which are also described: display of a parameter which indicates the degree of non-linearity; a means of automatically recognizing specific standardizing solutions; and a temperature-compensated algorithm for determining when a conductivity measurement signal is stable.

20 Claims, 1 Drawing Sheet

CALIBRATION PROCEDURE THAT IMPROVES ACCURACY OF ELECTROLYTIC CONDUCTIVITY MEASUREMENT SYSTEMS

BACKGROUND OF THE INVENTION

The present invention relates to improvements in systems for the measurement of electrolytic conductivity. Typically, these systems are used for the measurement of the conductivity of water and aqueous or non-aqueous solutions in environmental, industrial, medical, and other applications where an indication of the total ionic content of the sample liquid is desired. A typical system consists of a conductivity cell and meter. The meter applies an electrical input signal (generally a controlled voltage signal) to the cell which contacts the sample. The meter also senses a resultant output signal from the cell (generally a current signal) that is usually a linear function of the solution conductivity and a property of the cell called the cell constant.

There are many types of cells and meters. Typical cells may have two or four electrodes and may contain integral temperature sensors; cells may be dipped into solutions, solutions may be placed into cells, or solutions may flow through cells. Various meters may apply excitation signals differing in voltage, frequency, and waveform; they may display results with a digital or analog display; they may sense and display temperature; and they may perform various calculations in order to compensate automatically for the effect of temperature on the conductivity of various samples.

In order that the ensuing description be clearly understood, the following definitions are provided:

Conductivity is a bulk property of a material and represents quantitatively the capacity of that material to conduct electricity; its reciprocal is resistivity. Conductivity does not depend on the quantity, shape, or size of the conducting material. Earlier literature often uses the terms specific conductance and its reciprocal specific resistance in place of conductivity and resistivity. Common units of conductivity are siemens/cm (S/cm), millisiemens/cm (mS/cm), and microsiemens/cm ($\mu$S/cm).

Conductance is a property of a particular piece of material, i.e., a component or device. Its reciprocal is resistance. As an illustration of the difference between conductance and conductivity, consider two different pieces or pure copper wire: they may have different conductance values but will always have the same conductivity of the material, the conductivity of copper. Common units of conductance are siemens (S), millisiemens (mS), and microsiemens ($\mu$S).

The Cell Constant of an electrolytic conductivity cell is a conversion factor which converts conductance to conductivity. It has units of $cm^{-1}$. The cell constant is a function of cell geometry. In a two-electrode conductivity cell, the cell constant is a predictable function of the area of the electrodes and the distance between them, if the electrodes are non-polarized. It is useful to note that when the cell constant equals 1.0, the solution conductivity is equal to the cell conductance.

Polarization is a condition in which a resistance, not determined by the bulk resistance of the solution under test, exists at the interface between an electrode and the test solution. This is an undesirable phenomenon which causes errors in conductivity measurements. Conductivity cell and meter designers enact measures which eliminate or minimize electrode polarization. For example, on the meter side, AC excitation signals are virtually always used. This minimizes alteration of the ionic concentrations in the solution in the vicinity of the electrode surfaces. On the electrode side, materials such as platinum black are used. The catalytic nature of the platinum black surface facilitates electron transfer between the electrode and the solution.

Generally, a linear range of operation is specified for a conductivity system. This is the range of sample conductivity over which the cell output signal is linearly proportional to solution conductivity. Or, expressed differently, the linear range is the range over which the cell constant is truly a constant.

Conductivity systems must be calibrated. It is typical that the conductivity meter is calibrated at the point of manufacture and is able to convert the cell output signal to conductance without further calibration by the user, though he or she may wish to verify meter calibration using a standard resistor in place of the cell. The user must however carry out a procedure which serves to calibrate the conductivity cell. This is equivalent to determining the cell constant.

In the cell calibration step, the user places the cell in contact with a solution of known conductivity, often called a standard solution or simply a standard. The meter is then adjusted to display the known conductivity of that solution at the temperature of the measurement; alternatively, a cell constant value can be input into the meter such that the correct conductivity reading is displayed. This process is equivalent to defining a calibration curve; in this case, the curve is assumed to be a straight line. A line is defined by two points: here, one point is obtained through the assumption that an output signal of zero equals a conductivity of zero, and the second point is obtained in the calibration step. The calibration line is defined by the equation:

$$C = k * S_{raw}$$

Where c is the conductivity in appropriate units such as mS/cm, k is the cell constant and has units of $cm^{-1}$, and $S_{Raw}$ is the raw cell output signal in units of mS. This equation illustrates the role of the cell constant in converting the sample conductance value, $S_{raw}$, into a conductivity value, c.

Linearity of a conductivity system is an ideal. Typically, there is a range of sample conductivity values over which satisfactory linearity is observed for a given system. At the low end of the range, deviations from linearity can be ascribed to such factors as capacitive impedance, which in an AC measurement, increases at high resistances, i.e., low conductivities. At the high end of the conductivity range, the resistances of wiring and other components in measuring circuit become significant compared to the resistance of the cell. Also, at the high end of the range, the current through the cell is greater: this increases the tendency of the electrodes to become polarized.

SUMMARY OF THE INVENTION

Disclosed is a two-point calibration procedure using a mathematical algorithm that improves the accuracy of electrolytic conductivity measurements by correcting for non-linear behavior of conductivity cells.

Unlike purely mathematical means of correcting for non-linearity which may use second or higher order equations, this algorithm has the following advantages: it is based on an analysis of the physical phenomena which are responsible for non-linearity; it yields one unique solution, i.e., it uses an equation that has only one root; and it yields diagnostic information concerning the behavior of the cell.

In another embodiment of this invention, a conductivity system utilizing the described algorithm was built and tested. The testing of this system led to the development of the following system enhancements that are also deemed to be embodiments of the present invention:

- Built-in display of a parameter that indicates the degree of non-linearity;
- A means of automatically recognizing specific standardizing solutions; and
- A temperature-compensated algorithm for determining when a conductivity measurement signal is stable.

DETAILED DESCRIPTION OF THE INVENTION

Figure 1:
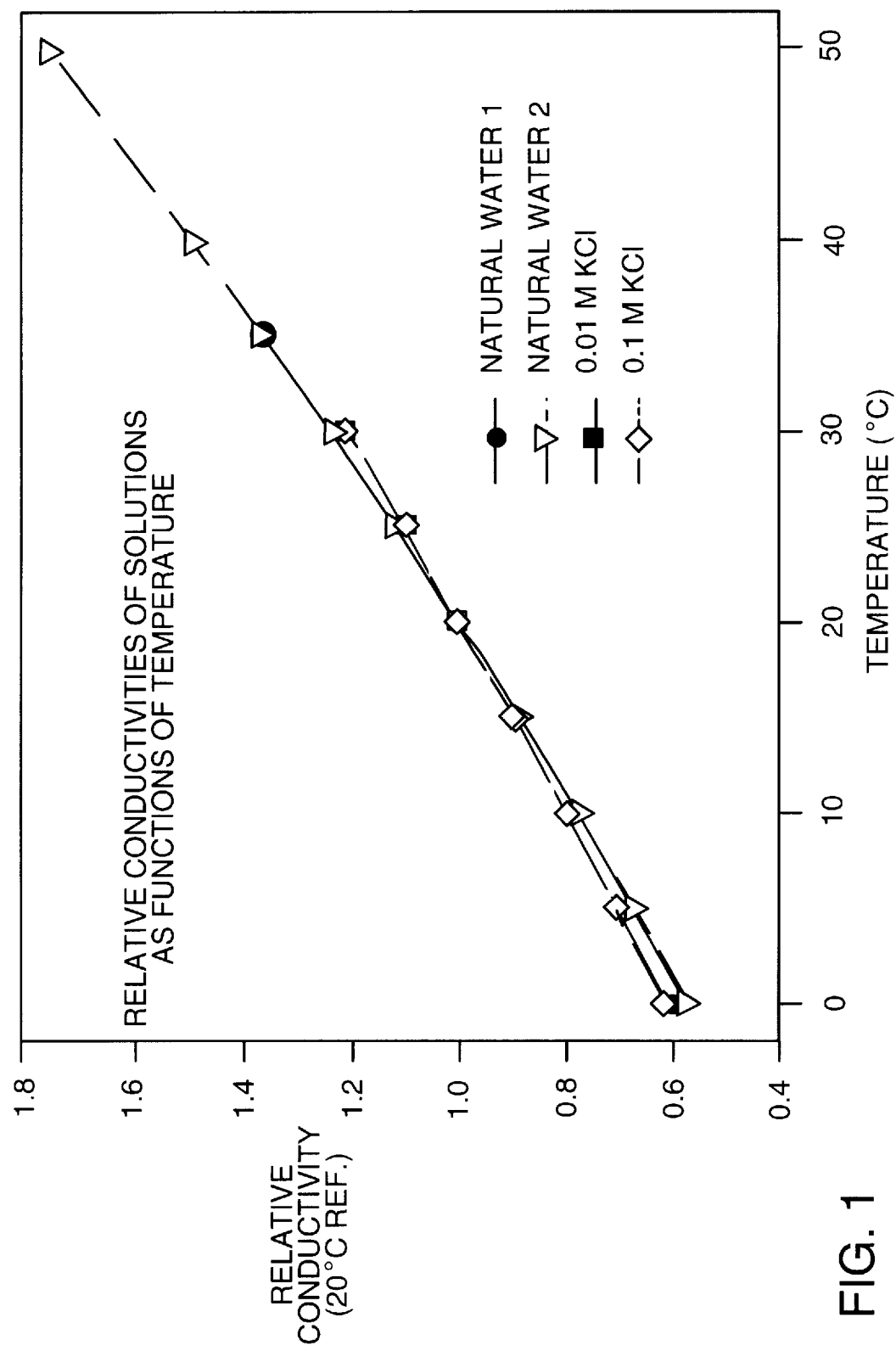
FIG. 1 shows plots of relative conductivity versus temperature for two KCl standards and for two typical natural water samples.

The present invention relates to the problem of electrode polarization limiting the useful range of conductivity cells. It arose from the study of planar conductivity cells which have a non-conventional geometry (for simplicity, the following explanation will be restricted to two-electrode cells). The advantage of these planar cells is that they can be fabricated using techniques developed to a high degree of sophistication and cost-effectiveness in the microelectronics industry: they are constructed on a "chip". The cell geometries are non-conventional in that the electrodes share a common sensing surface in contact with the sample, whereas conventional cells are generally configured such that the electrodes oppose each other and the sample solution is located between them.

When evaluating planar cells with platinum electrodes, non-linearity was observed at lower conductivities than with conventional electrode cells. In attempting to understand this phenomenon, it was hypothesized that the resistance of the contacts between the chip and connecting wires might be somewhat high, since soldering to the platinum might have been improperly executed; or, the connecting traces or electrodes on the chip itself were somewhat high in resistance, since they were composed of extremely thin layers of metal. Were this to be true, an undesirable "series resistance" would have been present in the measuring circuit, and its effect would have been to induce non-linearity at higher sample conductivity values. This hypothesis can be illustrated in a series of equations.

First:

$$R_{Total} = R_{Solution} + R_{Series} \quad (2)$$

where $R_{Total}$ is the total circuit resistance which is the sum of the solution resistance, $R_{Solution}$, and the undesirable series resistance, $R_{Series}$. The raw conductance signal, $S_{Raw}$, from equation (1) is in this case expressed by the following equation:

$$S_{raw} = \frac{1}{R_{Solution} + R_{Series}} \quad (3)$$

from which it follows that:

$$R_{Solution} = \frac{1 - S_{Raw} * R_{Series}}{S_{Raw}} \quad (4)$$

and combining with equation (1) gives:

$$c = k * \frac{1}{R_{Solution}} = \frac{k * S_{Raw}}{1 - S_{Raw} * R_{Series}} \quad (5)$$

Note the following:

1. $S_{Raw}$ as defined in equation (3), no longer represents the sample conductance as in equation (1), but rather the overall cell conductance which includes the effect of the series resistance, $R_{series}$.

2. A linear relationship no longer exists between $S_{Raw}$ and $R_{Solution}$, except when the series resistance, $R_{Series}$, is zero, in which case equation (5) reduces back to equation (1).

This hypothesis was tested in two experiments. The first experiment was based on the observation that equation (5) can be solved for k and $R_{Series}$ by means of the following equations if two solutions of known conductivity are tested. From equation (5), two equations can be written, one for each solution of known conductivity:

$$c1 = \frac{k * S1_{Raw}}{1 - S1_{Raw} * R_{Series}} \quad (6)$$

$$c2 = \frac{k * S2_{Raw}}{1 - S2_{Raw} * R_{Series}} \quad (7)$$

where c1 and $S1_{Raw}$ represent the known conductivity value and raw conductance signal respectively for the first known solution, and c2 and $S2_{Raw}$ represent the same parameters for the second. Subtraction of the second equation from the first yields a single equation from which the variable $R_{Series}$ is eliminated so that k can be calculated:

$$k = \frac{\frac{1}{S1_{Raw}} - \frac{1}{S2_{Raw}}}{\frac{1}{c1} - \frac{1}{c2}} \quad (8)$$

Rearrangement of equation (6) or (7) then allows calculation of $R_{Series}$:

$$R_{Series} = \frac{k * S1_{Raw} - c1}{-S1_{Raw} * c1} \quad (9)$$

If different pairs of solutions yielded similar values in this experiment, that would be an indication that a series resistance which was independent of solution conductivity did exist, and this would provide support for the hypothesis. Typical experimental results are shown in Table 1.

The results in TABLE 1 indicate that equation (5) does accurately describe the behavior of the planar conductivity cell. Using three solutions and calculating $R_{Series}$ three different ways yielded values which were very similar, supporting the hypothesis that a series resistance was present in the measuring circuit.

TABLE 1

| Solution Number | Composition | Known conductivity[a] ($\mu$S/cm) | Measured Conductance ($\mu$S) | k and $R_{Series}$ from Sol'ns 1 & 2[b] | k and $R_{Series}$ from Sol'ns 2 & 3[b] | k and $R_{Series}$ from Sol'ns 1 & 3[b] |
|---|---|---|---|---|---|---|
| 1 | $10^{-3}$ M KCl | 150.5 | 52.7 | 2.85<br>52.86 | 2.85<br>50.85 | 2.85<br>52.67 |
| 2 | $10^{-2}$ M KCl | 1413 | 483 | | | |
| 3 | $10^{-1}$ M KCl | 12860 | 3667 | | | |

[a]The conductivity values of solutions 1 and 2 were calculated based on values from the International Critical Tables and NIST; the conductivity of solution 3 was measured with a commercial cell with confirmed linearity in this conductivity range.
[b]k is in units of cm$^{-1}$ and $R_{Series}$ is in ohms.

The second experiment was to simply measure the resistance of the measuring circuit. This was done by immersing the planar cell in mercury. This simulates measurement of an electrolyte with a resistance close enough to zero to be negligible in the circuit, such that any resistance found would be equal to $R_{Series}$, which the first experiment indicated should be about 51 ohms. This experiment yielded a very surprising result: the series resistance value was found to be negligible.

This surprising result suggested that the phenomenon referred to as the series resistance was probably, in fact, polarization of the electrodes. When electrodes share a common surface, as in the planar cell, the current density tends to be non-uniform: higher at the edges which are closest to each other. This higher current density makes the electrodes more susceptible to polarization at sample conductivities lower than would induce polarization in conventional cells, and thus the linear range is restricted to lower conductivity values. This polarization resistance (more properly called "impedance", since it appeared in an AC measurement) is what was calculated from equation (9).

In view of these experiments, it was realized that the exercise of calculating the so-called series resistance after measurement of the conductance of two known solutions provided a means of "linearizing" non-ideal conductivity systems. Moreover, this linearizing algorithm is rational, i.e., it tells a user something about the system. While it is clear that a system could be linearized by using a second or higher order equation to fit non-linear data, however, that is a purely mathematical or statistical technique which is not derived from an analysis of electrochemical phenomena in the cell and does not give direct information concerning the degree of polarization in rational units such as ohms. Furthermore, a second or higher order equation is satisfied by two or more roots, giving rise to confusion and complexity, since additional algorithms are required to determine which root represents the conductivity of the real sample solution. In this case, the set of equations, (6) through (9), derived from equation (5), always yields a unique solution.

It is useful to mention that a series resistance or polarization is expected to induce a specific type of non-linearity, that is, where the conductivity value obtained in a solution of higher conductivity than that used for calibration is lower than expected. A value higher than expected would result in a series resistance value that is negative when calculated according to equations (6) through (9) and that is a physical impossibility. Perfectly linear calibration data would result in calculation of a series resistance value of zero, since the term $k*S1_{Raw}-c1$ in equation (9) would equal zero.

The usefulness of this calibration technique was first realized while studying non-conventional, planar conductivity cells which display non-linear characteristics at relatively low conductivity values. The technique is also useful with conventional cells, since they are not ideally linear and will show substantial non-linearity at high conductivity values. The technique allows the conventional cells to be accurate at higher conductivities than would otherwise be possible. The technique has diagnostic utility as well. For example, platinum conductivity electrodes are platinized to reduce polarization. From time to time the platinum surface degrades and must be replatinized. The data from the two-point calibration can be used to indicate when the polarization has increased beyond a specified degree by monitoring the value of the "series resistance" (more under Non-Linearity Parameter).

The use of equations (5) through (9) are not limited to a two-point calibration. A minimum of two points are required in order to solve for k and $R_{Series}$, but those familiar with numerical methods of algebra will recognize that techniques such as non-linear, least-squares regression enable one to obtain a "best fit" solution to a series of equations analogous to equations (6) and (7) when more than two calibration solutions are used.

Two-point conductivity cell calibration using the described algorithm to calculate the cell constant and so-called series resistance improves the accuracy of conductivity measurements. A prototype microprocessor-based meter was built and the calibration technique was tested and proven to be effective with both planar and conventional cells. Working with the prototype system suggested certain enhancements to the two-point calibration.

These enhancements, which are described below, were found not only to mitigate the inconvenience of having to run an additional solution, but were found also to stand alone as useful features of any conductivity meter, used with either planar or conventional cells.

ENHANCEMENTS

Non-Linearity Parameter

To many users, who are not electrochemists but need to use conductivity systems, the idea of "series resistance" or polarization is not meaningful. Therefore, a simpler concept, a parameter which might be called "%Linearity" or "%Slope" was devised.

It is instructive to describe an example of the utility of a diagnostic parameter such as %Linearity. It is common to use a solution of 0.01M KCl or 0.1M KCl as a single standard for carrying out a one-point conductivity cell calibration, i.e., for determining the cell constant. These solutions have conductivity values at 25° C. of 1,413 and 12,860 $\mu$S/cm respectively. With an ideally linear conductivity cell, the cell constant determined with either standard will be the same. Under these circumstances, if 0.01M KCl is used as the standard and the meter reading adjusted to 1,413 $\mu$S/cm, a reading of 12,860 $\mu$S/cm will be observed when 0.1M KCl is next measured. Some illustrative data is shown in TABLE 2.

Referring to TABLE 2, a raw conductance reading of 1,400 $\mu$S in the first standard results in a calculated cell constant of 1.009 cm$^{-1}$. When 12,600 $\mu$S, the raw conductance reading in 0.1M KCl, is multiplied by the cell constant to obtain the observed reading, it is found to be 12,717 $\mu$S/cm, slightly less than the 12,860 $\mu$S/cm expected for an ideal cell. A value of 99.5 is obtained for the parameter %Linearity, defined here by equation (10).

$$\% \text{ Linearity} = \frac{k - S2_{Raw}}{c2} * 100 \qquad (10)$$

TABLE 2

| | First Standard | | |
|---|---|---|---|
| Composition | Conductance Reading ($S1_{Raw}$, $\mu$S) | Conductivity Value (c1, $\mu$S/cm) | Calculated Cell Constant (k, cm) |
| 0.01 M KCl | 1,400 | 1,413 | 1.009 |

| | Second Standard | | | |
|---|---|---|---|---|
| Composition | Conductance Reading ($S2_{Raw}$ $\mu$S/cm) | Observed Reading (c, $\mu$S/cm) | Expected Reading (c2, $\mu$S/cm) | Calculated % Linearity |
| 0.1 M KCl | 12,600 | 12,717 | 12,860 | 99.5 |

A %Linearity value of 99.5 would in most cases be considered an indication that the one-point calibration in 0.01M KCl was satisfactory even for measurements in 0.1M KCl. The two-point calibration would improve performance by eliminating the 0.5% error that is indicated by a %Linearity value of 99.5, but the point of this example is to illustrate the following additional advantage to the two-point calibration.

As previously mentioned, platinized platinum cells degrade with time. The two-point calibration would indicate this degradation by an ever decreasing value for %Linearity. Users could incorporate into their standard operating procedures provisions that cells be replatinized when %Linearity values fall below a certain value such as 98 or 95%. Cells other than platinized platinum cells degrade with time due to fouling or other phenomena and the %Linearity concept that is offered by the two-point calibration would be of use in verifying proper operation of those cells as well. The %Linearity parameter is much more sensitive indicator of cell performance than the cell constant alone.

It is worth mentioning that perfectly linear calibration data would result in a %Linearity value of 100 since (k−$S2_{Raw}$)/c2 would equal one (series resistance of zero). It is possible that a %Linearity value greater than 100 could be obtained. This would result from some phenomenon other than a series resistance or polarization, for example, inaccurate standard solutions. In the prototype system, reversion to a one-point calibration occurred in this situation and an error message was displayed which suggested that the standard solutions might be bad.

Thus, after performing a two-point calibration, the prototype meter was programmed to display two calibration constants, the cell constant, k, and the %Linearity. It should be evident from the calibration and %Linearity equations that %Linearity is algebraically derivable from the value of the series resistance and vice versa.

Automatic Standard Recognition

Since at least two known solutions must be tested to correct for non-linearity, the described calibration procedure is somewhat more complex and time-consuming than a conventional one-point procedure. In order to mitigate this disadvantage, a feature was added which allowed automatic recognition of standard solutions.

The automatic standard recognition feature operates as follows: if the number of possible standard solutions which may be used is limited to a relative few with conductivity values that are in quite different ranges (as is usually the case), and if approximate cell constant and series resistance values are input to the meter or reside in memory as default values, and if the meter is set to a calibration mode so that it "knows" the cell is in a standard solution from a list contained in memory. This can be accomplished by means of a table or equation which matches the "estimated" conductivity value (a function of measured conductance and the approximate cell constant and series resistance) to that associated in memory with the appropriate standard at the temperature of measurement. Having identified the standard, the meter can then display the exact conductivity value at the measured temperature and the user can press a key to indicate acceptance of that value, which is then stored in memory and used in subsequent calibration calculations. This process eliminates the need for the user to look up the proper conductivity value for that standard and input it to the meter. The time and effort required to accomplish input of calibration data is thereby decreased.

In cases where the cell constant and series resistance values are not known accurately enough for recognition of the standard to take place, a "manual" calibration can be carried out first. The cell constant and series resistance values determined during this calibration can then be stored in memory and used to recognize standards in subsequent calibrations.

Although the foregoing description of standard recognition has been written with the two-point calibration in mind, it is applicable to less than or more than two standards.

In order for standard recognition to be viable, certain limitations must be imposed. For example, the accuracy of the estimated cell constant and series resistance values stored in memory determines the magnitude of conductivity differences that must exist between standards which are adjacent to each other in the list of standards to be identified. Otherwise misidentification could occur. Also, conductivity values for each listed standard as functions of temperature must be stored in memory, either by means of a table or equation which covers the range of temperature over which standard recognition is specified to work.

Temperature-Compensated Stability Algorithm

An additional enhancement to the prototype system was a temperature-compensated signal stability determination algorithm, henceforth referred to simply as the stability algorithm. The desirability of this feature was realized, in particular, when applying the standard recognition feature to planar cells. A common feature of instrumentation of this type is automatic monitoring of the rate of change of input signals, such that an indication of whether a signal is stable can be displayed. An example of such an indication might be the illumination of the word "READY" when the rate of change of the input signals is less than a specified value. Such a feature eliminates the need on the part of the user to make a judgment as to whether the signal is stable or not.

Since electrolytic conductivity is such a strong function of temperature (~2%/°C.), most cell and meter combinations include simultaneous temperature measurement by using a temperature sensor which is integral to the cell. Oftentimes, the temperature of a sample will be different from that of the sensing probe (by "probe" is meant the combination of cell and temperature sensor). When the probe is placed into the sample, the probe and sample in contact with the probe begin to change temperature.

In some cases, depending on probe design, the sensed temperature may or may not be the temperature which correctly represents the temperature of the conductivity measurement, because the relevant temperature for the conductivity measurement is that of the bulk solution contained in the measurement volume of the cell, whereas the temperature indicated by the temperature sensor is that of the sensor itself, which may be imbedded at some depth in the probe body and not be representative of the bulk solution temperature until a period of time sufficient for attaining complete temperature equilibration has elapsed. Since system designers recognize when the conductivity and temperature signals are changing, that there may be a disparity between the sensed temperature and the temperature relevant to the conductivity measurement, "READY" indications are generally not given until the rate of change of both the temperature and conductivity signals are less than specified values. This disparity represents one of two relevant cases and will henceforth be referred to as the "non-tracking" case.

In the particular case of a planar cell with a planar temperature sensor, the second relevant case, the "tracking" case, is encountered. Here, although the temperature changes when the probe is immersed into a sample, the conductivity electrodes and non-embedded temperature sensor are so thin that they rapidly assume sample temperature and change with it, so that the measured temperature does represent the temperature in the bulk solution where the conductivity is determined. The temperature signal "tracks" the conductivity signal. In this case, it would be desirable for a "READY" indicator to be activated even though both signals are changing, since the displayed conductivity and temperature values are correct, although changing.

Reading the conductivity and temperature values "on the fly", that is, while they are still changing but tracking each other, is especially useful when applying automatic standard recognition while using a planar cell. Reading on the fly decreases the time required to acquire a calibration point and in the two-point calibration this is doubly useful. In the prototype system, the meter automatically read and stored the calibration data when stability was sensed and then prompted the user to perform the next step. Initially, the conductivity and temperature signals were evaluated individually to determine stability. With a planar cell, it was found to take an inordinately long time, many minutes, for stability to be achieved when the sample temperature was different from room temperature. Thus a new stability algorithm was devised which was capable of determining whether the conductivity and temperature readings were tracking each other and which would take the readings on the fly when tracking was confirmed.

In order to determine whether conductivity and temperature signals are tracking, it is necessary to know how the conductivity of the solution in the cell changes with temperature, or to make some educated assumptions. In the case presented here, the standard solutions to be recognized were KCl solutions. Also, it was desired that the stability algorithm be able to sense the tracking situation in certain sample solutions as well. FIG. 1 shows plots or relative conductivity versus temperature for two KCl standards and for two typical natural water samples. As can be seen, the curves are similar but not identical. It was estimated, however, that a function derived from an average of the curves shown could be used to determine tracking with adequate accuracy, and the algorithm developed around this assumption is now described.

The rate of change of raw conductance signal can be expressed as its first derivative with respect to time, $dS_{Raw}/dt$. This value can be calculated in any number of ways from time-labeled conductance values which are stored in the meter's memory at regular, specified intervals. Likewise, a rate of change of temperature, $dT/dt$, can be calculated. In a non-temperature-compensated stability algorithm, such as that initially tried in the prototype system, the "READY" criterion was satisfied when the values of both of these parameters were below specified values (absolute values to be exact). In the temperature-compensated stability algorithm, instead of calculating $dT/dt$, a rate of change of a function of temperature is calculated, $dF/dt$. The function F was derived from the data in FIG. 1. F was chosen to be a power series in temperature:

$$F = a + b*T + c*T^2 + d*T^3 \tag{11}$$

The data used to generate the curves in FIG. 1 were fit by the method of least-squares regression to equation (11)[1]. This resulted in a function F that varied with temperature in exactly the same manner as the conductivity of a typical solution of KCl or natural water would. Now, instead of evaluating two rate of change functions to determine stability, a single ratio is evaluated:

[1] In the prototype system, it was actually the voltage output of a thermistor network that was fit to the equation; this results in different numerical values for the coefficients a, b, c, and d, but is in principle the same as fitting to a temperature value.

$$R = \frac{dS_{Raw}/dt}{dF/dt} = \frac{dS_{Raw}}{dF} \tag{12}$$

This ratio, R, does not change its value when the rate of change of conductivity and temperature values are tracking. The meter can thus compare a series of time-labeled R values in order to turn the "READY" indicator on or off, or in order to take and record the data during calibration.

Although developed specifically with the planar cell in mind, it was found that the use of the stability parameter R in place of individual conductivity and temperature stability parameters improved performance even with conventional cells. For example, in cases where the sample temperature is changing due to changes in ambient temperature or because the sample is taken from a sample source into a lab at a different temperature, algorithms which depend on both conductivity and temperature being stable may fail to show the "READY" indication even though "tracking" is occurring. With the temperature compensated algorithm, the "READY" indication was found to be a more reliable indicator of the stability of the measuring system.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method for calibrating the conductivity system of a conductivity meter, wherein the calibration method is for linearizing non-ideal conductivity system, comprising the steps of:

providing a probe comprising a conductivity cell;

contacting the probe with a first through $n^{th}$ known solution to provide a first through $n^{th}$ conductance value, where n is an integer $\geq 2$;

calculating the series resistance or polarization of the conductivity system from the n conductance values by solving the following equation for each of said values $$c_n = k * \frac{1}{R_{Solution}} = \frac{k * S_{nRaw}}{1 - S_{nRaw} * R_{Series}}$$

where $c_n$ is the conductivity of the $n^{th}$ solution, k is the cell constant and $S_{nRaw}$ is the raw cell output signal for the $n^{th}$ solution; and determining a linear calibration curve for said conductivity system using the results of said calculating step.

2. The method of claim 1, wherein n=2.

3. The method of claim 2, further comprising the step of:

calculating the %Linearity of the conductivity system by solving the following equation:

$$\% \text{ Linearity} = \frac{k - S2_{Raw}}{c2} * 100$$

4. The method of claim 1, wherein the probe further comprises temperature sensors, and said contacting step further for providing temperature values $t_n$.

5. The method of claim 4, further comprising the steps of providing a memory unit;

storing the values for $c_n$ and $t_n$ in said memory unit;

selectively utilizing said values for $c_n$ and $t_n$ for performing calibration.

6. The method of claim 1 wherein the conductivity cell is a planar cell.

7. The method of claim 1 wherein the conductivity cell is a conventional cell.

8. The method of claim 1 wherein the conductivity cell is provided with platinum electrodes.

9. The method of claim 4 wherein the conductivity cell is a planar cell.

10. The method of claim 9, further comprising the steps of:

calculating a power series function of the instantaneous temperature following the contacting step;

calculating a ratio of the instantaneous values of $S_{nRaw}$ to said instantaneous values of said power series;

indicating when the rate of change of said value of said ratio is beneath a predetermined threshold.

11. An apparatus for calibrating the conductivity system of a conductivity meter and for linearizing a non-ideal conductivity system, comprising:

a probe comprising a conductivity cell for measuring conductance values of solutions;

means for calculating the series resistance or polarization of the conductivity system from n conductance values by solving the following equation for each of said values $$c_n = k * \frac{1}{R_{Solution}} = \frac{k * S_{nRaw}}{1 - S_{nRaw} * R_{Series}}$$

where $c_n$ is the conductivity of the $n^{th}$ solution, k is the cell constant and $S_{nRaw}$ is the raw cell output signal for the $n^{th}$ solution; and means for determining a linear calibration curve for said conductivity system using the calculations of said calculating means.

12. The apparatus of claim 11, wherein n=2.

13. The apparatus of claim 12, further comprising:

means for determining the % Linearity of the conductivity system by solving the following equation:

$$\% \text{ Linearity} = \frac{k - S2_{Raw}}{c2} * 100$$

14. The apparatus of claim 11, wherein the probe further comprises temperature sensors for providing temperature values $t_n$ of the n solutions.

15. The apparatus of claim 14, further comprising a memory unit, said memory unit storing the values for $c_n$ and $t_n$; and means for selectively utilizing said values for $c_n$ and $t_n$ for performing calibration.

16. The apparatus of claim 11 wherein the conductivity cell is a planar cell.

17. The apparatus of claim 11 wherein the conductivity cell is a conventional cell.

18. The apparatus of claim 11 wherein the conductivity cell is provided with platinum electrodes.

19. The apparatus of claim 14 wherein the conductivity cell is a planar cell.

20. The apparatus of claim 19, further comprising:

means for calculating a power series function of the instantaneous temperature following the contacting step;

means for calculating a ratio of the instantaneous values of $S_{nRaW}$ to said instantaneous values of said power series;

an indicator for indicating when the rate of change of said value of said ratio is beneath a predetermined threshold.

* * * * *